United States Patent [19]

Tseng et al.

[11] Patent Number: 4,963,552

[45] Date of Patent: Oct. 16, 1990

[54] 1-SUBSTITUTE-1,2-DIHYDRO-4-((SUB-STITUTED)PHENYL)IMIDAZO-[1,5-A]PYRIMIDINE-8-CARBONITRILES

[75] Inventors: Shin S. Tseng, Bridgewater, N.J.; Herbert J. Brabander, Nanuet; Jannie S. Baker, White Plains; Joseph W. Epstein, Monroe, all of N.Y.

[73] Assignee: American Cyanamid Company, Wayne, N.J.

[21] Appl. No.: 399,097

[22] Filed: Aug. 28, 1989

[51] Int. Cl.$^5$ ............... A61K 31/495; A61K 31/445; C07D 487/06

[52] U.S. Cl. .................. 514/253; 514/233.2; 514/258; 544/117; 544/281

[58] Field of Search .................. 544/117, 281; 514/233.2, 253, 258

[56] References Cited

U.S. PATENT DOCUMENTS

| | | | |
|---|---|---|---|
| 4,178,449 | 12/1979 | Dusza et al. | 544/281 |
| 4,236,005 | 11/1980 | Dusza et al. | 544/281 |
| 4,847,256 | 7/1989 | Tseng et al. | 544/281 |

FOREIGN PATENT DOCUMENTS 3060985  3/1988  Japan ................... 544/281

*Primary Examiner*—Cecilia Shen
*Attorney, Agent, or Firm*—Kenneth J. Dow

[57] ABSTRACT

This disclosure describes 1-substituted-1,2-dihydro-4-[substituted)phenyl]imidazo[1,5-a]pyrimidine-8-carbonitriles which are useful as antihypertensive agents and/or as antidepressant agents in mammals.

19 Claims, No Drawings

1-SUBSTITUTE-1,2-DIHYDRO-4-((SUBSTITUTED)-PHENYL)IMIDAZO-[1,5-A]PYRIMIDINE-8-CARBONITRILES

BACKGROUND OF THE INVENTION

1. Field of the Invention

This invention relates to substituted imidazo[1,5-a]pyrimidine-carbonitriles useful as antihypertensive agents and/or antidepressant agents in mammals.

2. Description of the Prior Art

U.S. Pat. No. 4,178,449 and U.S. Pat. No. 4,236,005 to Dusza et al. describe pyrazolo[1,5-a]pyrimidines and imidazo[1,5-a]pyrimidines useful as anti-anxiety agents.

BRIEF SUMMARY OF THE INVENTION

The present invention relates to new organic compounds and more particularly is concerned With novel 1-substituted-1,2-dihydro-4-[(substituted)phenyl-]imidazo[1,5-a]pyrimidine-8-carbonitriles which are useful as antihypertensive agents and/or as antidepressant agents in mammals. The compounds of the present invention may be represented by the following structural formula I:

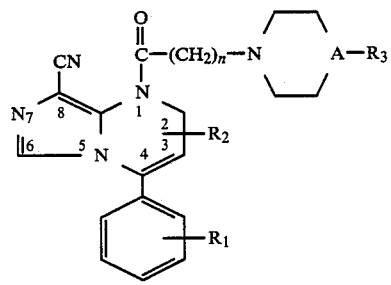

wherein n is an integer from 1 to 4 inclusive; $R_1$ represents a mono- or disubstituent selected from the group consisting essentially of hydrogen, lower alkyl($C_1$-$C_3$), lower alkoxy($C_1$-$C_3$), halogen, nitro, cyano and trifluoromethyl; $R_2$ is hydrogen or lower alkyl($C_1$-$C_3$); A is selected from the group consisting essentially of carbon, oxygen or nitrogen; with the proviso that when A is oxygen $R_3$ cannot exist; when A is carbon, $R_3$ is selected from hydrogen or phenyl and when A is nitrogen, $R_3$ is selected from the group consisting essentially of: phenyl, benzyl, (3-methoxyphenyl)methyl, (4-chlorophenyl)methyl, 3-phenoxypropyl, (4-chlorophenyl)-phenylmethyl, (2,6-dichlorophenyl)methyl, 2-pyridinyl, 2-chlorophenyl, 4-chlorophenyl, 4-methoxyphenyl, 2-furanylcarbonyl, 3-furanylcarbonyl alkoxycarbonyl, where alkoxy is ($C_1$-$C_3$), 2-propynyl, bis(4-fluorophenyl)methyl, 2-cyclohexylethyl, 1-methylethyl and 4-fluorophenyl and the pharmacologically acceptable acid addition salts thereof.

For purposes of this invention halogen may be selected from chlorine and iodine. Also included within the purview of the present invention are compounds of the formula:

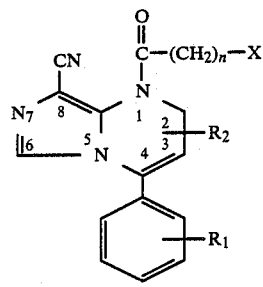

wherein n, $R_1$ and $R_2$ are as hereinabove described and X is a halide such as chlorine or iodine; said compounds being useful as intermediates for the preparation of the novel 1-substituted-1,2-dihydro-4-[(substituted)phenyl-]imidazo[1,5-a]pyrimidine-8-carbonitrile compounds described hereinabove.

The present invention also pertains to new compositions of matter containing the above defined novel compounds which compositions of matter are useful as antihypertensive agents and/or as antidepressant agents in mammals. The invention is also concerned with methods for treating hypertension or depression in mammals with the claimed compounds and to the chemical synthesis of the novel compounds disclosed herein. For the purposes of this invention the free bases are equivalent to their non-toxic acid-addition salts. The acid-addition salts of the organic bases of the present invention are, in general, relatively soluble in water, methanol and ethanol but relatively insoluble in non-polar organic solvents such as diethyl ether, benzene, toluene and the like.

The organic bases of this invention form nontoxic acid-addition salts with a variety of pharmacologically acceptable organic and inorganic salt-forming reagents. Thus, acid-addition salts, formed by admixture of the organic free base with one or more equivalents of an acid, suitably in a neutral solvent, are formed with such acids as sulfuric, phosphoris, hydrochloric, hydrobromic, maleic, sulfanic, citric, lactic, malic, succinic, tartaric, acetic, benzoic, fumaric, gluconic, ascorbic and the like.

DETAILED DESCRIPTION OF THE INVENTION

The novel compounds of the present invention are in general obtainable as white, off-white, yellow or tan crystalline solids having characteristic melting points and absorption spectra. They are generally soluble in organic solvents such as lower alkanols, chloroform, ethyl acetate, dichloromethane, tetrahydrofuran and the like, but are generally insoluble in water.

The novel 1-substituted-1,2-dihydro-4-[substituted)phenyl]imidazo[1,5-a]pyrimidine-8-carbonitriles of the present invention may be readily prepared as set forth in the following reaction schemes:

Scheme 1

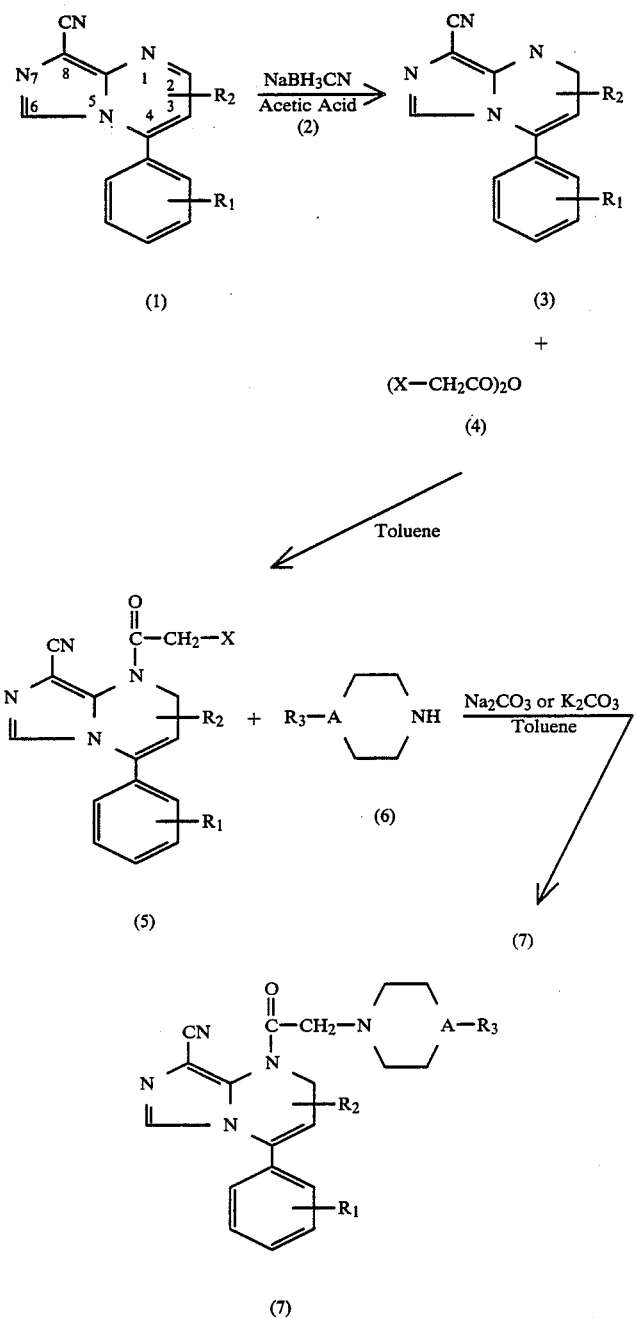

wherein R₁, R₂, R₃, A and X are as hereinabove defined.

In accordance with Scheme 1, an imidazo[1,5-a]pyrimidine (1) with an electron withdrawing group such as cyano and the like in the C₈ position and a substituted phenyl such as 3-(trifluoromethyl)phenyl and the like in the C₄ position is prepared as described in U.S. Pat. Nos. 4,178,449 and 4,236,005, hereby incorporated by reference, and reacted with sodium cyanoborohydride (2) by stirring in glacial acetic acid under nitrogen in an ice bath for approximately one hour, then at room temperature for 1–48 hours. Evaporation of the solvent in vacuo gives a solid which is dissolved in an inert solvent such as dichloromethane or acetonitrile and the like and treated with saturated sodium bicarbonate. The 1,2-dihydro-4-[(substituted)phenyl-]imidazo[1,5-a]pyrimidine-8-carbonitrile compound (3) is recovered by evaporation of the organic phase and is purified by conventional means. The dihydro compound (3) is mixed with a haloacetic anhydride (4) such as chloroacetic anhydride and the like and then added to a solvent such as toluene and the like. The stirred reaction mixture is heated at reflux under nitrogen for about 1½ hours, then is stirred at room temperature for about 2½ hours. The solvent is evaporated in vacuo and the solid is treated with ether to precipitate the 1-(haloalkanoyl)-1,2-dihydro-4-[(substituted)phenyl-]imidazo[1,5-a]pyrimidine-8-carbonitrile intermediate compounds (5) which are recrystallized by conventional means using solvents such as ethyl acetate/hexane and the like.

The 1-(haloalkanoyl)-1,2-dihydro-4-[(substituted)-phenyl]imidazo[1,5-a]pyrimidine-8-carbonitrile intermediate (5) is then reacted with an appropriate piperazine (6) in a solvent such as toluene and the like in the presence of an alkaline carbonate such as sodium or potassium carbonate and the like by heating at the reflux temperature for 4–30 hours, then filtering the mixture while hot and recovering the desired 1-substituted-1,2-dihydro-4-[(substituted)phenyl]imidazo[1,5-a]pyrimidine-8-carbonitrile product (7) by in vacuo evaporation of the filtrate. Further purification by conventional means may be employed using silica gel and solvents such as ethyl acetate, ether and the like.

tetrahydrofuran at ambient temperature for one hour then at the reflux temperature for about 4 hours, followed by filtration while hot. Evaporation of the filtrate provides the 1-haloalkanoyl)-12-dihydro-4-[(substituted)phenyl]imidazo[1,5-a]pyrimidine-8-carbonitrile intermediate compound (9). The intermediate (9) is then reacted with an appropriate piperazine (10) in a solvent such as toluene and the like in the presence of an alkaline carbonate such as sodium or potassium carbonate and the like by heating at the reflux temperature for 4–30 hours, then filtering the mixture while hot and evaporating the filtrate in vacuo to obtain the desired 1-substituted-1,2-dihydro-4-[(substituted)phenyl]imidazo[1,5-a]pyrimidine-8-carbonitrile product (11) which may be further purified by conventional means using silica gel and solvents such as acetate, ether and the like.

Scheme 2

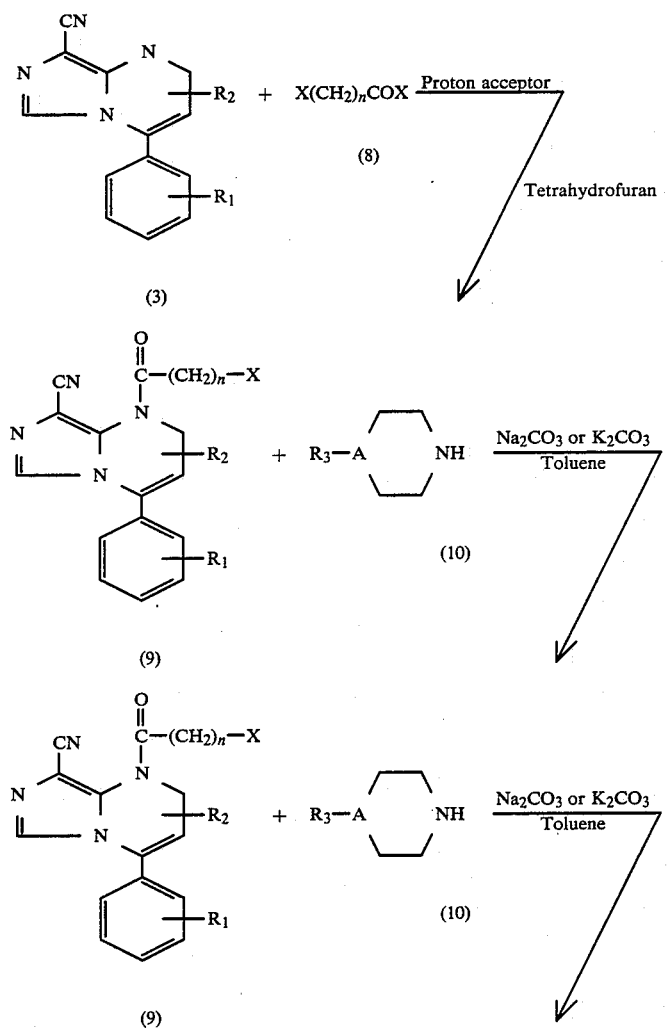

In the foregoing Scheme II, n, $R_1$, $R_2$, $R_3$, A and X are as hereinbefore defined In accordance with Scheme 2, a 1,2-dihydro-4-[(substituted)phenyl]imidazo[1,5-a]pyrimidine-s-carbonitrile (3) as described in Scheme 1 is mixed with a proton acceptor such as [1,8-bis(dimethylamino)naphthalene, N,N,N',N'-tetramethyl-1,8-naphthalenediamine] in an inert solvent such as dry tetrahydrofuran. This mixture is then reacted under nitrogen with a haloalkanoyl halide, e.g., 3-chloropropionyl chloride and the like, in dry In accordance with Schemes 1 and 2, when A is oxygen both compound 6 in Scheme 1 and compound 10 in Scheme 2 are morpholine; when A is carbon both compound 6 in Scheme 1 and compound 10 in Scheme 2 may be piperidine or 4-phenylpiperidine.

Representative samples of the novel compounds of the present invention have been shown to be active hypotensive agents at non-toxic doses when administered to mammals. These compounds were tested for hypotensive activity by the method of P. S. Chan and D. W. Poorvin, Clinical and Experimental Hypertension, 1 (6), 817–830 (1979). Male, 16 week old, spontaneously hypertensive rats of the Okamoto strain having an average mean arterial blood pressure of 160±1.5 mm of mercury are used in the test. One to three rats are used per test compound. The test compound is suspended in 2% pre-boiled starch at a concentration of 50 mg/ml, and a rat is dosed by gavage at a dose of 100 mg/kg of body weight or less, with 0.9% sodium chloride loading at a dose of 25 ml/kg of body weight. A second identical dose of the test compound, without sodium chloride loading, is given 24 hours later. At 28 hours after the initial dose the mean arterial blood pressure is measured by the method of Chan and Poorvin vide supra. The procedure is repeated in a second and third rat when necessary.

The results of this test on representative compounds of the present invention appear below in Table I.

TABLE I

Reduction of Mean Arterial Blood Pressure in spontaneously Hypertensive Rats

| Compound | Dose mg/kg | MABP/mm Hg (No. of rats) |
|---|---|---|
| 1-[[(5-Chloro-2-methoxyphenyl)-amino]acetyl]-1,2-dihydro-4-[3-(trifluoromethyl)phenyl]imidazo-[1,5-a]pyrimidine-8-carbonitrile | 100 | 135(3) |
| 1,2-Dihydro-1-[[4-(3-phenoxypropyl)-1-piperazinyl]acetyl]-4-[3-(trifluoromethyl)phenyl]imidazo-[1,5-a]pyrimidine-8-carbonitrile | 100 | 130(1) |
| 1-[[4-[(4-Chlorophenyl)phenylmethyl]-1-piperazinyl]acetyl]-1,2-dihydro-4-[3-(trifluoromethyl)-phenyl]imidazo[1,5-a]-8-carbonitrile | 100 | 137(1) |
| 1-[[4-(4-Chlorophenyl)-1-piperazinyl]acetyl]-1,2-dihydro-4-[3-(trifluoromethyl)phenyl]imidazo-[1,5-a]pyrimidine-8-carbonitrile | 100 | 137(1) |
| 1,2-Dihydro-1-[(4-phenyl-1-piperidinyl)acetyl]-4-[3-(trifluoromethyl)phenyl]imidazo[1,5-a]-pyrimidine-8-carbonitrile | 100 | 137(4) |
| 1,2-Dihydro-1-[[4-(2-propynyl)-1-piperazinyl]acetyl]-4-[3-(trifluoromethyl)phenyl]imidazo[1,5-a]pyrimidine-8-carbonitrile, dihydrochloride | 100 | 129(3) |
| 1-[3-[4-(4-Fluorophenyl)-1-piperazinyl]-1-oxopropyl]-1,2-dihydro-4-[3-(trifluoromethyl)phenyl]-imidazo[1,5-a]pyrimidine-8-carbonitrile | 100 | 110(1) |
| 1,2-Dihydro-1-[1-oxo-3-(4-phenyl-1-piperzinyl)propyl]-4-[3-(trifluoromethyl)phenyl]imidazo[1,5-a]-pyrimidine-8-carbonitrile | 100 | 115(1) |
| 1-[3-[4-(4-Chlorophenyl)-1-piperaziny]-1-oxopropyl]-1,2-dihydro-4-[3-(trifluoromethyl)phenyl]-imidazo[1,5-a]pyrimidine-8-carbonitrile | 100 | 118(1) |
| 4-[3-[8-Cyano-4-[3-trifluoromethyl)phenyl]imidazo[1,5-a]pyrimidin-1(2H)-yl]-3-oxopropyl]-1-piperazinecarboxylic acid, ethyl ester, monohydrochloride | 100 | 134(2) |
| 1-[3-[4-[(4-Chlorophenyl)methyl]-1-piperazinyl]-1-oxopropyl]-1,2-dihydro-4-[3-(trifluoromethyl)-phenyl]imidazo[1,5-a]pyrimidine-8-carbonitrile | 100 | 128(1) |
| 1,2-Dihydro-1-[3-[4-(1-methylethyl)-1-piperazinyl]-1-oxopropyl]-4-[3-trifluoromethyl)phenyl]-imidazo[1,5-a]pyrimidine-8-car- | 50 | 133(3) |

TABLE I-continued

Reduction of Mean Arterial Blood Pressure in spontaneously Hypertensive Rats

| Compound | Dose mg/kg | MABP/mm Hg (No. of rats) |
|---|---|---|
| bonitrile | | |

The activity of the compounds of this invention as antidepressant agents was verified in the following test which measures the ability of a test compound to inhibit [$^3$H]-imipramine binding to human platelet membranes.

Platelet membranes were obtained using the procedure described by Wennogle, L. P., et al., Pharmac. Biochem Behav., 15, 975 (1981). Fresh human platelet concentrates(less than 48 hours old) were obtained from the New York Blood Center. These concentrates were prepared in a citrate-dextrose anticoagulant using standard techniques. Platelets were washed twice by centrifugation (2500 x G, 10 minutes) in 50 volumes of an antiprotease buffer containing 0.005M potassium chloride, 0.12M sodium chloride, 0.05M Tris pH 7.5, 0.025 Units/ml aprotinin, 0.5 μg/m pepstatin, 2×10$^5$M bacitracin, 3 mM ethylenediaminetetraacetic acid and 1.0 mM ethylene glycol-bis(β-aminoethyl ether)-N,N'-tetraacetic acid. Antiproteases have been shown to inhibit the breakdown of the [$^3$H]-imipramine receptor [Wennogle, L. P., et al. (vide supra)]. All procedures were conducted at 0° C. using plastic laboratory ware throughout the platelet membrane preparation. Platelets were resuspended in 20 volumes of buffer and sonicated 3 times using 10 second bursts of a Branson sonifier (cell disrupter 350) at setting 6 (standard ¾ inch horn), keeping the sample on ice throughout the procedure. Platelet membranes were then washed twice at 18,000 x G for 20 minutes with 50 volumes of the antiprotease buffer and resuspended to 3.0 mg protein/ml using the Bradford protein analysis with bovine gamma globulin as standard. Membranes were used immediately or stored frozen in liquid nitrogen.

The displacement of [$^3$H]-imipramine binding to human platelet membranes was performed essentially as described by Paul, S. M., et al, Life Sci., 26, 953 (1980) with the following modifications. Membranes (0.3 mg protein) were suspended in antiprotease buffer with both 3.0 mM [$^3$H]-imipramine (New England Nuclear) and displacing drug or buffer in a total volume of 250 μl in glass test tubes. Samples were incubated for 90 minutes at 0° C., then diluted to 5 ml in 0.12 mM sodium chloride, 0.005M potassium chloride, 0.05 Tris pH 7.5 (wash buffer) and immediately filtered through GF/B Whatman Filters and washed twice with 5 ml of wash buffer. Filters were counted in a liquid scintillation counter after addition of Beckman Hp Scintillant.

Non-specific binding of [$^3$H]-imipramine was defined as that fraction (generally 35%) of radioactivity that was not displaced by 10 μm desmethylimipramine. Specific binding was determined by subtraction of this non-specific level from values for total [$^3$H]-imipramine binding which were measured by incubating [$^3$H]-imipramine in the absence of displacing drug. Compounds were tested in duplicate test tubes at a concentration of 10 μm. Compounds which inhibited binding by more than 50% were considered to be active.

The results of this test on representative compounds of this invention appear in Table II.

TABLE II

[³H]-Imipramine Binding to Human Platelet Membranes

| Compound | % Inhibition |
| --- | --- |
| 1,2-Dihydro-1-[[4-[(3-methoxyphenyl)methyl]-1-piperzinyl]acetyl]-4-[3-(trifluoromethyl)phenyl]imidazo[1,5-a]pyrimidine-8-carbonitrile, dihydrochloride | 75 |
| 1-[[4-[(4-Chlorophenyl)methyl]-1-piperazinyl]acetyl]-1,2-dihydro-4-[3-(trifluoromethyl)phenyl]imidazo[1,5-a]pyrimidine-8-carbonitrile | 93 |
| 1,2-Dihydro-1-[[4-(3-phenoxypropyl)-1-piperazinyl]acetyl]-4-[3-(trifluoromethyl)phenyl]imidazo[1,5-a]pyrimidine-8-carbonitrile | 50 |
| 1-[[4-[(4-Chlorophenyl)methyl]-1-piperazinyl]acetyl]-1,2-dihydro-4-[3-(trifluoromethyl)phenyl]imidazo[1,5-a]pyrimidine-1-carbonitrile | 92 |
| 1,2-Dihydro-1-[[4-[(3-methoxyphenyl)methyl]-1-piperazinyl]acetyl]-4-[3-(trifluoromethyl)phenyl]imidazo[1,5-a]pyrimidine-8-carbonitrile | 81 |
| 1-[[4-[(4-Chlorophenyl)methyl]-1-piperazinyl]acetyl]-1,2-dihydro-4-[3-(trifluoromethyl)phenyl]imidazo[1,5-a]pyrimidine-8-carbonitrile | 80 |
| 1-[3-[4-(4-Fluorophenyl)-1-piperzinyl]-1-oxopropyl]-1,2-dihydro-4-[3-(trifluoromethyl)phenyl]imidazo[1,5-a]pyrimidine-8-carbonitrile | 78 |
| 1-[3-[4-(4-Chlorophenyl)-1-piperazinyl]-1-oxopropyl]-1,2-dihydro-4-[3-(trifluoromethyl)phenyl]imidazo[1,5-a]pyrimidine-8-carbonitrile | 53 |
| 1-[3-[4-[(4-Chlorophenyl)methyl-1-piperazinyl]-1-oxopropyl]-1,2-dihydro-4-[3-(trifluoromethyl)phenyl]imidazo[1,5-a]pyrimidine-1-carbonitrile | 75 |
| 1,2-Dihydro-1-[1-oxo-3-[4-(3-phenoxypropyl)-1-piperzinyl]propyl]-4-[3-(trifluoromethyl)phenyl]imidazo[1,5-a]pyrimidine-8-carbonitrile | 66 |
| 1,2-Dihydro-1-[1-oxo-3-[4-(phenylmethyl)-1-piperazinyl]propyl]-4-[3-(trifluoromethyl)phenyl]imidazo[1,5-a] pyrimidine-8-carbonitrile | 61 |
| 1-[3-[4-[(2,6-Dichlorophenyl)methyl]-1-piperazinyl]-1-oxopropyl]-1,2-dihydro-4-[3-(trifluoromethyl)phenyl]imidazo[1,5-a]-pyrimidine-8-carbonitrile | 98 |

The novel compounds of the present invention appear to be highly useful for lowering elevated blood pressure or alleviating depression in mammals when administered in amounts ranging from about 2.5 mg to about 100 mg/kg of body weight per day. A preferred dosage regimen for optimum results would be from about 50 mg to about 750 mg per dose. Such dosage units are employed that a total of from about 200 mg to about 3.0 g of the active compound for a subject of about 70 kg of body weight are administering in a 24 hour period.

The dosage regimen for the above-described utilities may be adjusted to provide the optimum therapeutic response. For example, several divided doses may be administered daily or the dose may be proportionally reduced as indicated by the exigencies of the therapeutic situation. A decided practical advantage is that these active compounds may be administered in any convenient manner such as by the oral, intravenous, intramuscular or subcutaneous routes.

The active compounds may be administered orally, for example, with an inert diluent or with an assimilable edible carrier. They may be enclosed in hard or soft shell gelatin capsules or compressed into tablets. They also may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 50 and 500 mg of active compound.

The tablets, troches, pills, capsules and the like may also contain the following: A binder such as gum tragacant h, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule it may contain, in addition to materials of the above type, a liquid carrier. Various other materials may be present as coatings or to otherwise modify the physical form of the dosage unit. For instance, tablets, pills or capsules may be coated with shellac, sugar or both, syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained release preparations and formulations.

The active compounds may also be administered parentally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The invention will be described in greater detail in conjunction with the following non-limiting examples.

Example 1

1,2-Dihydro-4-[3-(trifluoromethyl)phenyl]imidazo[1,5-a]pyrimidine-8-carbonitrile To a stirred mixture of 1.0 g of 4-(α,α,α-trifluoro-m-tolyl)imidazo[1,5-a]pyrimidine-8-carbonitrile (prepared as described in U.S. Pat. No. 4,236,005, Ex. 28) in 100 ml of methyl alcohol under nitrogen, at room temperature, was added, one at a time, 3 pellets of sodium borohydride, totaling about 300 mg. The mixture was stirred until the sodium borohydride was consumed and then was allowed to stand at room temperature. The precipitate which formed was filtered off and set aside (A). The filtrate was evaporated to dryness in vacuo. Water was added to the residue. Then the mixture was extracted with dichloromethane. The organic solution was dried over anhydrous sodium sulfate and passed through a short column of hydrous magnesium silicate. Evaporation of the eluate with the addition of hexane gave crystals (B). The preceding precipitate (A) and the crystals (B) were combined and recrystallized from ethanol to give 350 mg of the product of the example as colorless crystals, mp 248°–250° C.

Example 2

1,2-Dihydro-4-[3-(trifluoromethyl)phenyl]imidazo[1,5-a]pyrimidine-8-carbonitrile To a stirred mixture of 10.0 g of 4-(α,α,α-trifluoro-m-tolyl)imidazo[1,5-a]pyrimidine-8-carbonitrile (prepared as described in U.S. Pat. No. 4,236,005, Ex. 28) in 150 ml of glacial acetic acid, under nitrogen, at ice bath temperature, was added portionwise 4.15 g of sodium cyanoborohydride. The reaction mixture was stirred in the cold for 30 minutes then at room temperature for 2½ hours. Then about 50 ml of water was added to the reaction mixture. The precipitate was collected by filtration, washed with water and dried in vacuo to give 8.8 g of the desired product, mp 241°–243° C.

Example 3

1-(Chloroacetyl)-1,2-dihydro-4-[3-(trifluoromethyl)phenyl]imidazo[1,5-a]pyrimidine-8-carbonitrile A mixture of 9.4 g of 1,2-dihydro-4-[3-(trifluoromethyl)phenyl]imidazo[1,5-a]pyrimidine-8-carbonitrile (prepared as described in Example 2) and 16.0 g of chloroacetic anhydride in 200 ml of toluene, under nitrogen, was heated under reflux with stirring for 1½ hours, then was stirred at room temperature for 2 hours. The precipitate was collected by filtration, washed with ether and dried to give 2.2 g of crude product (A).

The toluene-ether filtrate and wash was concentrated to an oil, then 25 ml of ether was added with seeds from product (A). The mixture was scratched, then allowed to stand at room temperature for 16 hours. The mixture was treated with 25 ml of ether, then the crystals were collected and washed twice with ether to give 5.8 g of additional product (B).

A total of 5.8 g of combined products (A) and (B) above was recrystallized from ethyl acetate-hexane to give 4.45 g of the desired product as white crystals, mp 140°–142° C.

Example 4

1-(3-Chloro-1-oxopropyl)-1,2-dihydro-4-[3-(trifluoromethyl)phenyl]imidazo[1,5-a]pyrimidine-8-carbonitrile To a stirred mixture of 4.5 g of 1,2-dihydro-4-[3-(trifluoromethyl)phenyl]imidazo[1,5-a]pyrimidine-8-carbonitrile (prepared as described in Example 2) and 3.6 g of [1,8-bis(dimethylamino)naphthalene-N,N,N',N'-tetramethyl-1,8-naphthalenediamine] in 120 ml of dry tetrahydrofuran at room temperature, under nitrogen was added over a period of 12–15 minutes a solution of 3.9 g of 3-chloropropionyl chloride in 30 ml of dry tetrahydrofuran. The mixture was stirred at room temperature under nitrogen for one hour then under reflux for 4 hours. The solution was filtered hot and the filtrate was evaporated to dryness in vacuo. The residue was triturated with anhydrous ether and gave 5.95 g of the product of the example as an off-white solid. The product was recrystallized from ethyl acetate, mp 165° 166° C.

Example 5

1,2-Dihydro-1-[[4-[(3-methoxyphenyl)methyl]-1-piperazinyl]acetyl]-4-[3-(trifluoromethyl)phenyl]imidazo[1,5-a]pyrimidine-8-carbonitrile A mixture of 800 mg of 1-[3-methoxyphenyl)methyl]-piperazine, 1.2 g of 1-(chloroacetyl)-1,2-dihydro-4-[3-(trifluoromethyl)phenyl]imidazo[1,5-a]pyrimidine-8-carbonitrile and 450 mg of sodium carbonate in 50 ml of toluene was heated at reflux for 18 hours, then allowed to stand at room temperature. The mixture was treated with 10 ml of 1N sodium hydroxide and the phases were separated. The aqueous phase was extracted twice with chloroform. The organic phases were combined, washed with saturated sodium chloride solution, dried over anhydrous sodium sulfate, filtered and concentrated to obtain a viscous oil. The oil was treated with 15 ml of ether and scratching to separate tan crystals. The crystals were collected, washed with ether and dried. The dried material was dissolved in 15 ml of ethyl acetate with heating, then the solution was filtered. The filtrate was mixed with 30 ml of n-hexane and stored in a refrigerator until crystals formed. The product was collected by filtration, pressed to remove solvent then washed with hexane and dried in vacuo to give 1.25 g of the desired product, mp 131°–133° C.

Example 6

1,2-Dihydro-1-[[4-[(3-methoxyphenyl)methyl]-1-piperazinyl]acetyl]-4-[3-trifluoromethyl)phenyl]imidazo[1,5-a]pyrimidine-8-carbonitrile, dihydrochloride A 600 mg portion of 1,2-dihydro-1-[[4-[3-methoxyphenyl)methyl]-1-piperazinyl]acetyl]-4-[3-(trifluoromethyl)phenyl]imidazo[1,5-a]pyrimidine-8-carbonitrile (Example 5) was dissolved in 8.0 ml of ethyl acetate and filtered. The filtrate was acidified with 3.0 ml of 2.94N alcoholic hydrochloric acid. The precipitate which formed was collected, washed with ether and dried to give the product of the example as white crystals, mp 219°–221° C.

Example 7

1,2-Dihydro-1-[[4-(phenylmethyl)-1-piperazinyl]acetyl]-4-[3-(trifluoromethyl)phenyl]imidazo[1,5-a]pyrimidine-8-carbonitrile A stirred mixture of 1.6 g of 1-benzylpiperazine, 2.9 g of 1-(chloroacetyl)-1,2-dihydro-4-[3-(trifluoromethyl)phenyl]imidazo[1,5-a]pyrimidine-8-carbonitrile and 1.1 g of sodium carbonate in 55 ml of toluene was heated at reflux for 18 hours. The reaction mixture was cooled, then shaken with 20 ml of 1N sodium hydroxide. The layers were separated and the aqueous phase was extracted once with chloroform. The toluene phase above, and the chloroform extract were combined and washed with saturated sodium chloride solution, dried over anhydrous sodium sulfate, filtered and concentrated to obtain a viscous oil. The oil was dissolved in 50 ml of chloroform and passed through hydrous magnesium silicate. The chloroform filtrate was concentrated to an oil. The oil was heated to solution in 25 ml of ethyl acetate and filtered. Then 25 ml of n-hexane was added to the filtrate to crystallize the product. The crystals were collected by filtration, pressed to remove solvent, washed with hexane and dried to give 3.4 g of the product of the example as cream colored crystals, mp 167°–169° C.

Example 8

1,2-Dihydro-1-[[4-(phenylmethyl)-1-piperazinyl]acetyl]-4-[3-(trifluoromethyl)phenyl]imidazo[1,5-a]pyrimidine-8-carbonitrile, monohydrochloride A 1.7 g amount of 1,2-dihydro-1-[[4-(phenylmethyl)-1-piperazinyl]acetyl]-4-[3-(trifluoromethyl)phenyl]imidazo[1,5-a]pyrimidine-8-carbonitrile (Example 7) was dissolved in 50 ml of ethyl alcohol with heating. The solution was cooled and acidified with 7.0 ml of 2.94N alcoholic hydrochloric acid. Then an excess of ether was added. The precipitate was collected, washed with ether and dried. The solid was dissolved by heating in 75 ml of ethanol. The solution was filtered, then the filtrate was chilled to recrystallize 1.0 g of the desired product as white crystals, mp 225°–227° C.

Example 9

1,2-Dihydro-1-[[4-(3-phenoxypropyl)-1-piperazinyl acetyl]-4-[3-(trifluoromethyl)phenyl]imidazo[1,5-a]primidine-8-carbonitrile A stirred mixture of 1.7 g of 1-(chloroacetyl)-1,2-dihydro-4-[3-(trifluoromethyl)phenyl]imidazo]1,5-a]pyrimidine-8-carbonitrile, 940 mg of 3-phenoxypropyl piperazine and 680 mg of potassium carbonate in 50 ml of toluene was heated at reflux for 18 hours. The reaction mixture was cooled, then shaken with 50.0 ml of 1N sodium hydroxide. The layers were separated. The organic layer (A) was washed with water, then dried over anhydrous sodium sulfate. The basic aqueous layer and the aqueous wash were combined and extracted with chloroform. The chloroform extract (B) was washed with water then dried over anhydrous sodium sulfate. Organic solutions (A) and (B) were combined and evaporated to dryness in vacuo to give a gummy solid. The solid was dissolved by heating with 25% ethyl acetate in hexane. The hot solution was filtered and the filtrate was concentrated on the steam bath. The addition of hexane precipitated an oily film which was collected by decantation. The decantation procedure with hexane was repeated three times. The combined oily precipitate was dissolved in about 10 ml of ethyl alcohol then 10 ml of 3.4N alcoholic hydrochloric acid was added. About 25 ml of ether was added and the crystals that formed were collected and washed with ether. This material was dried in vacuo to give 1.43 g of a solid, mp 251°–252° C.

The solid was treated with a mixture of 15 ml of 10N sodium hydroxide and 10 ml of water in ethyl acetate. The organic layer was dried over anhydrous sodium sulfate, passed through a short column of silica and evaporated in vacuo to give the product of the example as 1.17 g of a white solid, mp 234°–235° C.

Example 10

1-[[4-[(4-Chlorophenyl)phenylmethyl]-1-piperazinyl]acetyl]-1,2-dihydro-4-[3-(trifluoromethyl)phenyl]imidazo[1,5-a]pyrimidine-8-carbonitrile A mixture of 1.53 g of 1-(chloroacetyl)-1,2-dihydro-4-[3-(trifluoromethyl)phenyl]imidazo[1,5-a]pyrimidine-8-carbonitrile, 1.32 g of N-(p-chlorobenzhydryl)piperazine and 990 mg of [1,8-bis(dimethylamino)naphthalene, N,N,N′,N′-tetramethyl-1,8-naphthalenediamine] in 60 ml of toluene was stirred and heated at reflux for 17 hours. The reaction mixture was filtered hot. The filtrate was cooled, then shaken with 50.0 ml of 1N sodium hydroxide and worked up by the procedure of Example 7 to obtain a viscous oil. The oil in ethyl acetate was passed through a silica column to give a solid upon evaporation of the solvent. The solid was dissolved in 40% ethyl acetate/hexane and again passed through a short silica column. Evaporation of the solvent in vacuo gave 2.00 g of the desired product as a yellow solid, mp 105°–107° C.

Following the general procedures of Examples 5–10 and using the intermediates of Example 3 and 4 with the indicated piperazine, the products of Examples 11–24 found in Table III were obtained.

TABLE III

| Ex. | Intermediate | Piperazine | Product | MP °C. |
|-----|--------------|------------|---------|--------|
| 11 | Ex. 3 | 4-chlorobenzyl | 1-[[4-[(4-Chlorophenyl)methyl]-1-piperazinyl]-acetyl]-1,2-dihydro-4-[3-(trifluoromethyl)-phenyl]imidazo[1,5-a]pyrimidine-8-carbonitrile | 107–109 |
| 12 | Ex. 3 | 4-chlorobenzyl | 1-[[4-[(4-Chlorophenyl)methyl]-1-piperazinyl]-acetyl]-1,2-dihydro-4-[3-(trifluoromethyl)-phenyl]imidazo[1,5-a]pyrimidine-8-carbo-nitrile, dihydrochloride | 242–244 |
| 13 | Ex. 3 | 4-chlorophenyl | 1-[[4-[(4-Chlorophenyl)-1-piperazinyl]acetyl]-1,2-dihydro-4-[3-(trifluoromethyl)phenyl]-imidazo[1,5-a]pyrimidine-8-carbonitrile | 114–115 |
| 14 | Ex. 3 | N-propargyl | 1,2-Dihydro-1-[[4-(2-propynyl)-1-piperazinyl]-acetyl]-4-[3-(trifluoromethyl)phenyl]imidazo-[1,5-a]pyrimidine-8-carbonitrile, dihydro-chloride | 189–190 |
| 15 | Ex. 3 | 4,4′-difluoro- | 1-[[4-[Bis(4-fluorophenyl)methyl]-1-pipera- | 126–127 |

TABLE III-continued

| Ex. | Intermediate | Piperazine | Product | MP °C. |
|---|---|---|---|---|
| | | benzhydryl | zinyl]acetyl]-1,2-dihydro-4-[3-(trifluoromethyl)phenyl]imidazo[1,5-a]pyrimidine-8-carbonitrile | |
| 16 | Ex. 4 | 4-fluorophenyl | 1-[3-[4-(4-Fluorophenyl)-1-piperazinyl]-1-oxopropyl]-1,2-dihydro-4-[3-(trifluoromethyl)phenyl]imidazo[1,5-a]pyrimidine-8-carbonitrile | 160–161 |
| 17 | Ex. 4 | N-phenyl | 1,2-Dihydro-1-[1-oxo-3-(4-phenyl-1-piperazinyl)propyl]-4-[3-(trifluoromethyl)phenyl]imidazo[1,5-a]pyrimidine-8-carbonitrile | 163–164 |
| 18 | Ex. 4 | 4-chlorophenyl | 1-[3-[4-(4-Chlorophenyl)-1-piperazinyl]-1-oxopropyl]-1,2-dihydro-4-[3-(trifluoromethyl)phenyl]imidazo[1,5-a]pyrimidine-8-carbonitrile | 146–147 |
| 19 | Ex. 4 | carboxylic acid, ethyl ester | 4-[3-[8-Cyano-4-[3-(trifluoromethyl)phenyl]imidazo[1,5-a]pyrimidine-1(2H)-yl]-3-oxopropyl]-1-piperazinecarboxylic acid, ethyl ester monohydrochloride | 225 |
| 20 | Ex. 4 | 4-chlorobenzyl | 1-[3-[4-[(4-Chlorophenyl)methyl]-1-piperazinyl]-1-oxopropyl]-1,2-dihydro-4-[3-(trifluoromethyl)phenyl]imidazo[1,5-a]pyrimidine-8-carbonitrile | 143–144 |
| 21 | Ex. 4 | 3-phenoxypropyl | 1,2-Dihydro-1-[1-oxo-3-[4-(3-phenoxypropyl)-1-piperazinyl]propyl]-4-[3-(trifluoromethyl)phenyl]imidazo[1,5-a]pyrimidine-8-carbonitrile | 148–149 |
| 22 | Ex. 4 | N-benzyl | 1,2-Dihydro-1-[1-oxo-3-[(4-phenylmethyl)-1-piperazinyl]propyl]-4-[3-(trifluoromethyl)phenyl]imidazo[1,5-a]pyrimidine-8-carbonitrile | 160–161 |
| 23 | Ex. 4 | 2,6-dichlorobenzyl | 1-[4-[4-[(2,6-Dichlorophenyl)methyl]-1-piperazinyl]-1-oxopropyl]-1,2-dihydro-4-[3-(trifluoromethyl)phenyl]imidazo[1,5-a]pyrimidine-8-carbonitrile | 188–190 |
| 24 | Ex. 4 | N-isopropyl | 1,2-Dihydro-1-[3-[4-(1-methylethyl)-1-piperazinyl]-1-oxopropyl]-4-[3-(trifluoromethyl)phenyl]imidazo[1,5-a]pyrimidine-8-carbonitrile | 161–162 |

Example 25

1,2-Dihydro-1-[[(4-phenyl-1-piperidinyl)acetyl]-4-[3-(trifluoromethyl)phenyl]imidazo[1,5-a]pyrimidine-8-carbonitrile A mixture of 1.30 g of 1-(chloroacetyl)-1,2-dihydro-4-[3-(trifluoromethyl)phenyl]imidazo[1,5-a]pyrimidine-8-caronitrile, 680 mg of 4-phenylpiperidine and 1.60 g of sodium carbonate in 50 ml of toluene was heated at the reflux temperature for about 23 hours. The reaction mixture was cooled and filtered. The filtrate was evaporated to dryness in vacuo. The residue was dissolved in about 25 ml of hot ethyl acetate. The solution was filtered over silica gel contained in a 50 ml coarse filter funnel. The filtrate was evaporated in vacuo to give 1.33 g of the desired product as a light yellow solid, mp 174°–175° C.

We claim:
1. A compound selected from those of the following formula:

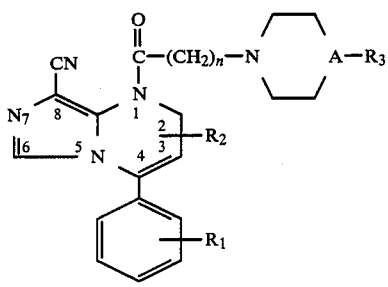

wherein n is an integer from 1 to 4 inclusive; $R_1$ represents a mono- or disubstituent selected from the group consisting essentially of hydrogen, lower alkyl($C_1$–$C_3$), lower alkoxy($C_1$–$C_3$), halogen, nitro, cyano and trifluoromethyl; $R_2$ is hydrogen or lower alkyl($C_1$–$C_3$); A is selected from the group consisting essentially of carbon, oxygen and nitrogen; with the proviso that when A is oxygen, $R_3$ cannot exist; when A is carbon, $R_3$ is selected from hydrogen or phenyl and when A is nitrogen, $R_3$ is selected from the group consisting essentially of phenyl, benzyl, (3-methoxyphenyl)methyl, (4-chlorophenyl)methyl, 3-phenoxypropyl, (4-chlorophenyl)phenylmethyl, (2,6-dichlorophenyl)methyl, 2-pyridinyl, 2-chlorophenyl, 4-chlorophenyl, 4-methoxyphenyl, 2-furanylcarbonyl, 3-furanylcarbonyl alkoxycarbonyl , where alkoxy is ($C_1$–$C_3$), 2-propynyl, bis(4-fluorophenyl)methyl, 2-cyclohexylethyl, 1-methylethyl and 4-fluorophenyl or the pharmacologically acceptable acid addition salts thereof.

2. The compound according to claim 1, 1,2-di-hydro-1-[[4-(3-phenoxypropyl)-1-piperazinyl]acetyl]-4-[3-(trifluoromethyl)phenyl]imidazo[1,5-a]pyrimidine-8-carbonitrile.

3. The compound according to claim 1, 1-[[4-[(4-chlorophenyl)phenylmethyl]-1-piperazinyl]acetyl]-1,2-dihydro-4-[3-(trifluoromethyl)phenyl]imidazo[1,5-a]pyrimidine-8carbonitrile.

4. The compound according to claim 1, 1-[[4-[(4-chlorophenyl)methyl]-1-piperazinyl]acetyl]-1,2-dihydro-4-[3-(trifluoromethyl)phenyl]imidazo[1,5-a]pyrimidine-8-carbonitrile.

5. The compound according to claim 1, 1-[[4-(4-chlorophenyl)-1-piperazinyl]acetyl]-1,2-dihydro-4-[(3-(trifluoromethyl)phenyl]imidazo[1,5-a]pyrimidine-8-carbonitrile.

6. The compound according to claim 1, 1,2-dihydro-1-[[4-(3-methoxyphenyl)methyl]-1-piperazinyl]acetyl]-4-[3-(trifluoromethyl)phenyl]imidazo[1,5-a]pyrimidine-8-carbonitrile.

7. The compound according to claim 1, 1,2-dihydro-1-[(4-phenyl-1-piperidinyl)acetyl]-4-[3-(trifluoromethyl)phenyl]imidazo[1,5-a]pyrimidine-8-carbonitrile.

8. The compound according to claim 1, 1,2-dihydro-1-[[4-(2-propynyl)-1-piperazinyl]acetyl]-4-[3-(trifluoromethyl)phenyl]imidazo[1,5-a]pyrimidine-8-carbonitrile.

9. The compound according to claim 1, 1-[3-[4-(4-fluorophenyl)-1-piperazinyl]-1-oxopropyl]-1,2-dihydro-4-[3-(trifluoromethyl)phenyl]imidazo[1,5-a]pyrimidine-8-carbonitrile.

10. The compound according to claim 1, 1,2-dihydro-1-[1-oxo-3-(4-phenyl-1-piperazinyl)propyl]-4-[3-(trifluoromethyl)phenyl]imidazo[1,5-a]pyrimidine-8-carbonitrile.

11. The compound according to claim 1, 1-[3-[4-[4-chlorophenyl)-1-piperazinyl]-1-oxopropyl]-1,2-dihydro-4-[3-(trifluoromethyl)phenyl]imidazo[1,5-a]-pyrimidine-8-carbonitrile.

12. The compound according to claim 1, 1,4-[3-[8-cyano-4-[3-(trifluoromethyl)phenyl]imidazo[1,5-a]pyrimidin-1(2H)-yl]-3-oxopropyl]-1-piperazinecarboxylic acid, ethyl ester, monohydrochloride.

13. The compound according to claim 1, 1-[3-[4-[(4-chlorophenyl)methyl]-1-piperazinyl]-1-oxopropyl]-1,2-dihydro-4-[3-(trifluoromethyl)phenyl]imidazo[1,5-a]pyrimidine-8-carbonitrile.

14. The compound according to claim 1, 1,2-dihydro-1-[1-oxo-3-[4-(3-phenoxypropyl)-1-piperazinyl]propyl]-4-[3-(trifluoromethyl)phenyl]imidazo[1,5-a]pyrimidine-8-carbonitrile.

15. The compound according to claim 1, 1-3-[4-[(2,6-dichlorophenyl)methyl]-1-piperazinyl]-1-oxopropyl]-1,2-dihydro-4-[3-(trifluoromethyl)phenyl]imidazo[1,5-a]pyrimidine-8-carbonitrile.

16. A method of lowering elevated blood pressure in a mammal which comprises administering internally to said mammal an effective hypotensive amount of a compound of claim 1.

17. A method of treating depression in a mammal which comprises administering internally to said mammal an effective antidepressant amount of a compound of claim 1.

18. A pharmaceutical composition for the treatment of hypertension or depression in mammals which comprises 5 to 500 mg of a compound of claim 1 in association with a pharmaceutically acceptable carrier, diluent, or excipient 19. A composition according to claim 18 in unit dosage form.

* * * * *